United States Patent [19]

Kunstmann et al.

[11] 4,049,655
[45] Sept. 20, 1977

[54] 1,4-DIHYDRO-2H-ISOQUINOLINE DERIVATIVES

[75] Inventors: Rudolf Kunstmann, Hofheim, Taunus; Joachim Kaiser, Bad Soden, Taunus, both of Germany

[73] Assignee: Hoechst Aktiengesellschaft, Frankfurt am Main, Germany

[21] Appl. No.: 679,784

[22] Filed: Apr. 23, 1976

Related U.S. Application Data

[62] Division of Ser. No. 515,659, Oct. 17, 1974, Pat. No. 3,980,655.

[30] Foreign Application Priority Data

Oct. 20, 1973 Germany .............................. 2352702
Sept. 14, 1974 Germany .............................. 2444109

[51] Int. Cl.² .................. C07C 413/06; A61K 31/535
[52] U.S. Cl. ................................... 424/248.5; 544/128
[58] Field of Search ................. 260/247.1 L; 424/248, 424/248.5

[56] References Cited

U.S. PATENT DOCUMENTS 3,980,655 9/1976 Kunstmann et al. .............. 260/247.1

Primary Examiner—Henry R. Jiles
Assistant Examiner—R. W. Ramsuer
Attorney, Agent, or Firm—Curtis, Morris & Safford

[57] ABSTRACT 1,4-Dihydro-2H-isoquinoline derivatives of the general formula I

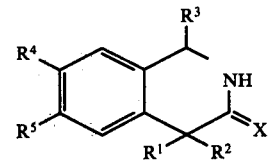

in which
R[1] represents hydrogen or straight chain or branched alkyl of 1 to 6 carbon atoms,
R[2] represents low molecular dialkylaminoalkyl, in which both alkyl groups of the dialkylamino group together with the nitrogen atom may also form a 5-, 6- or 7-membered saturated ring in which one carbon atom may be substituted by an oxygen atom, a sulfur atom or another nitrogen atom which may be substituted by hydrogen, $C_1$–$C_4$-alkyl or phenyl, or R[1] and R[2] together may form a 5- or 6-membered saturated ring containing 1 nitrogen atom,
R[3] represents phenyl which may be mono- or di-substituted by halogen, nitro, amino or sulfamoyl, or acylamino or alkyl each containing 1 to 4 carbon atoms, or pyridyl,
R[4] and R[5], which may identical or different, represent hydrogen or alkoxy of 1 to 4 carbon atoms, and
X represent oxygen or sulfur, their physiologically tolerated salts, process for preparing them. The compounds are active on the coronary circulation and are distinguished in particular by an anti-arrhythmic action and may, therefore, be used in the treatment of disorders of the heart rhythm.

4 Claims, No Drawings

1,4-DIHYDRO-2H-ISOQUINOLINE DERIVATIVES

This is a division of application Ser. No. 515,659, filed Oct. 17, 1974 now U.S. Pat. No. 3,980,655.

1-Phenyl-1,4-dihydro-2H-isoquinoline-3-ones which are unsubstituted or dimethyl substituted in the 4-position are known from Acad. Sci. Hung. 60, (1969), page 177, and 1-alkyl-1,4-dihydro-2H-dihydro-2H-isoquinoline-3-ones which are unsubstituted or di-lower alkyl substituted in the 4position are known from U.S. Pat. No. 3,480,634. 1-Phenyl-1,4-dihydro-2H-isoquinoline-3-ones which are alkyl-substituted in the 4-position and their anticonvulsive action are described in Belgian Pat. No. 784,037.

Now, we have found that 1,4-dihydro-2H-isoquinoline-3-ones which carry basic substituents in the 4-position and phenyl or pyridyl substituents in the 1-position have an action on the coronary circulation.

Thus, the present invention relates to 1,4-dihydro-2H-isoquinoline derivatives of the general formula I (I)

in which
 $R^1$ represents hydrogen or straight chain or branched alkyl of 1 to 6 carbon atoms,
 $R^2$ represents low molecular dialkylaminoalkyl, in which both alkyl groups of the dialkylamino group together with the nitrogen atom may also form a 5-, 6- or 7-membered saturated ring in which one carbon atom may be substituted by an oxygen atom, a sulfur atom or another nitrogen atom which may be substituted by hydrogen, $C_1-C_4$-alkyl or phenyl, or $R^1$ and $R^2$ together may form a 5- or 6-membered saturated ring containing 1 nitrogen atom,
 $R^3$ represents phenyl which may be mono- or di-substituted by halogen, nitro, amino or sulfamoyl, or acylamino (e.g. alkamoylamino) or alkyl each containing 1 to 4 carbon atoms, or pyridyl,
 $R^4$ and $R^5$, which may identical or different, represent hydrogen or alkoxy of 1 to 4 carbon atoms, and
 X represents oxygen or sulfur,
and to their physiologically tolerated salts.

Among the radicals mentioned above, $R^1$ preferably represents hydrogen, $R^2$ preferably represents a dialkylaminoalkyl group of the formula $$-(CH_2)_n-N\diagdown_Y^Z$$

in which n preferably represents the number 2 or 3 and Z and Y are identical hydrocarbon radicals of 1 to 4 carbon atoms or Z and Y together with the nitrogen atom form a 5- or 6-membered ring, furthermore the morpholino-ethyl radical, $R^3$ represents a phenyl ring mono- or di-substituted by chlorine, amino or sulfamyl, or the pyridine radical, and $R^4$ and $R^5$ represent identical substituents, hydrogen or methoxy groups being preferred.

Furthermore, the present invention relates to a process for preparing the above-specified compounds and to pharmaceutical preparations produced with these compounds.

Thus, the process for preparing the compounds of the invention comprises a. reacting compounds of the formula II (II)

in which $R^1$, $R^2$, $R^4$ and $R^5$ have the meanings given for formula I and Q represents a —CN or —CXNH$_2$ groups, in which X is oxygen or sulfur, with an aldehyde of the formula III $$R^3 — CHO \qquad (III)$$

in which $R^3$ has the meaning given for formula I, to compounds of the formula I, or b. hydrogenating compounds of the formula IV (IV)

in which $R^1$ to $R^5$ and X have the meanings given for formula I, or c. subjecting oximes of the formula V (V)

in which $R^1$ to $R^5$ have the meanings given for formula I, or their O-derivatives, to a Beckmann rearrangement, or d. reacting compounds of the formula VI (VI)

in which $R^1$ to $R^5$ have the meanings given for formula I, with ammonia or salts thereof, or e. cyclizing α-hydroxyacetic acid amides or -thioamides of the formula VII (VII)

-continued

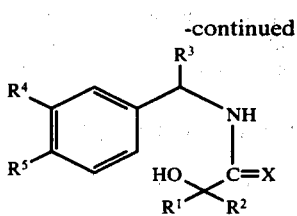

in which $R^1$ to $R^5$ and X have the meanings given for formula I, or f. cyclizing amino-acid- or thioamino-acid derivatives of the formula VIII (VIII)

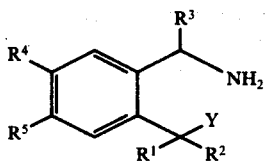

in which $R^1$ to $R^5$ have the meanings given for formula I and Y represents a carboxyl or thio-carboxyl group, or the derivatives thereof, or hydroxy-carboxylic acid amides or hydroxy-thiocarboxylic acid amines of the formula IX (IX)

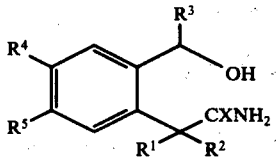

in which $R^1$ to $R^5$ and X have the meanings given for formula I, or g. cyclizing metal organyles of the formula X (X)

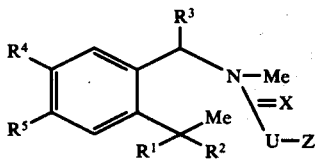

in which $R^1$ to $R^5$ and X have the meanings given for formula I, U represents oxygen, sulfur or the NH-group, Z represents alkyl or aryl, Me represents a mono-valent alkali metal, with separation of Me U Z, or h. cyclizing benzylidene-bisphenyl-acetic acid amides or benzylidene-bis-thiophenylacetic acid amides of the formula XI (XI)

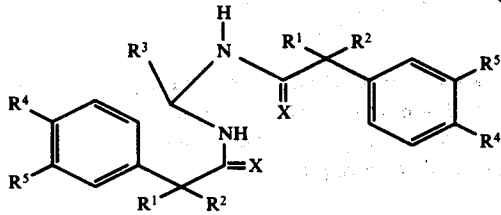

in which $R^1$ to $R^5$ and X have the meanings given for formula I, with separation of a phenyl- or thio-phenyl-acetic acid amide, or i. subsequently introducing into compounds of the formula I in which $R^1$ and/or $R^2$ represent hydrogen, the substituents $R^1$ and/or $R^2$ by alkylation, or k. reacting compounds of the formula XII

XII

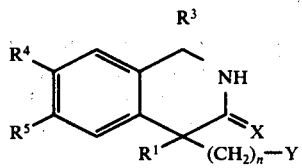

in which X, $R^1$, $R^3$, $R^4$ and $R^5$ have the meanings given for formula I and in which n is a number from 1 to 4 and Y represents a substituent which is replaceable by a secondary amine, with a secondary amine, or l. subsequently substituting the amino group in a compound of the formula XIII (XIII)

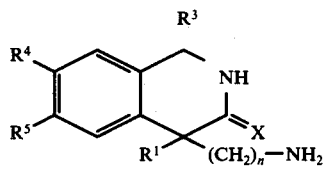

in which $R^1$, $R^3$ to $R^5$ and X have the meanings given for formula I, and n is a number from 1 to 4, or m. cyclizing a compound of the formula XIV

XIV

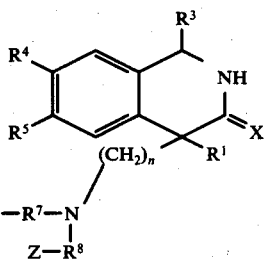

in which X, $R^1$, $R^3$, $R^4$ and $R^5$ have the meanings given for formula I, n is a number from 1 to 4, $R^7$ and $R^8$ represent low molecular alkyl and Y and Z represent the hydroxy, mercapto or amino group, or n. cyclizing a compound of the formula XIV, in which X, $R^1$, $R^3$, $R^4$, $R^5$, $R^7$, $R^8$ and n have the meanings given above and Y and Z represent a radical which may be substituted by ammonia, a primary amine, hydrogen sulfide or water, with ammonia, a primary amine or by a treatment with water or hydrogen sulfide, and, if desired, replacing oxygen in the reaction products by sulfur, or sulfur by oxygen in a known manner.

The benzyl-cyanides of the general formula II (Q = CN) may be prepared, for example by alkylation of the corresponding benzyl-cyanides with an alkyl halide in the presence of sodium amide in an inert solvent, for example according to the method described in Liebigs Annalen, Vol. 561 (1949), page 52 et seq.

The benzyl-cyanides so obtained are reacted with an aldehyde (III) in the presence of acid catalysts with or without a solvent. As catalysts, there may be used in particular mineral acids, for example sulfuric acid, hydrochloric acid and phosphoric acid, Lewis acids such as boron trifluoride and aluminum chloride, and phosphorus-oxychloride. As solvents, there may be used, for example benzene, toluene, carbon tetrachloride or trichloroethylene.

The reaction is carried out, for example according to the method described in Acta Chim. Acad. Sci. Hung. 60, page 177 (1969). Thus, both reactants are reacted in phosphoric acid, the content of phosphorus pentoxide of which may vary between that of 85% phosphoric acid and that of poly-phosphoric acid. The operation is carried out at temperatures in the range of from room temperature to 150° C, a temperature of from 90° to 110° C being preferred.

The phosphoric acid preferably used in the reaction is most simply prepared by adding 30 to 70 g of phosphorus pentoxide to 30 to 70 ml of 85% phosphoric acid.

The reaction of the aldehydes III with phenylacetic acid amides of the formula II (Q = —CO—NH$_2$) is likewise carried out most advantageously in the same manner.

The thioamides of the formula II (Q = —CSNH$_2$) are prepared according to the usual methods from phenylacetic acid amides by exchange of the oxygen for sulfur. The condensation with an aldehyde of the formula III is effected under the same conditions as described above.

The starting compounds IV which are used in method (b) are obtained, for example according to the method described in J. Heterocyclic Chem. 1, (1970), page 615, by subjecting compounds of the formula XII to the reactions in the order indicated therein.

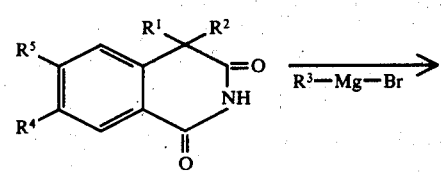
(XV)

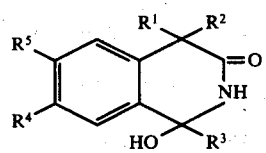
(XVI)

CH$_3$OH/HCl ↓

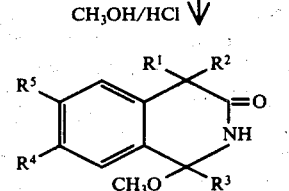
(XVII)

—CH$_3$OH →

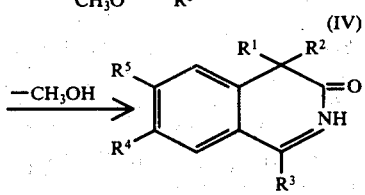
(IV)

By reaction with a Grignard reagent, there is obtained from XII the hydroxy compound XIII which is reacted with methanol/hydrochloric acid to the methyl ether XIV.

After separation of methanol, there is obtained IV in which X = oxygen. The corresponding thio-compund is obtained by replacing the oxygen of the lactam group in a compound of formula XVII by sulfur in one of the usual ways and subsequently separating methanol as described above.

The reduction of IV to I may be carried out catalytically in the presence of metal catalysts, for example Raney nickel or palladium black in suitable solvents, for example alcohol or ether. Suitable complex hydrides may also be used for the reduction. The operation is carried out, for example, with sodium boron hydride in solvents, for example methanol, dioxane or dimethoxyethane, at temperatures between room temperature and the boiling point of the solvent.

The oximes of the formula V required for method (c) are obtained according to the method described in J. Chem. Soc. (C), page 2245 (1970).

This method is started from suitably substituted indane-2-ones XVIII

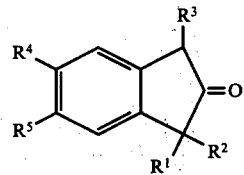
(XVIII)

in which R$^1$ to R$^5$ have the meanings given above, which are reacted to the oximes V in the usual manner.

As O-derivatives of the oximes, there may be used in particular the mesylates or tosylates thereof, which are prepared in the usual way.

The Beckmann rearrangement according to method (c) is effected suitably under acidic conditions or, in the case of substituted oximes, also under alkaline conditions.

The compounds of the formula VI are obtained, for example, by condensation of phenylacetic acid esters with aromatic aldehydes.

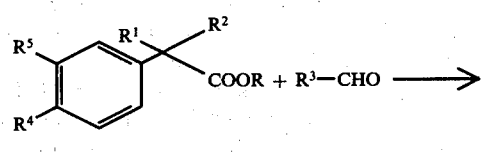

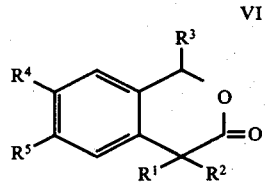
VI

This is effected by reacting the two reactants, with or without a solvent, for example acetic acid or tetrahydrofurane, with acid catalysts, for example sulfuric acid or hydrochloric acid, at temperatures between 25° C and 100° C. Compounds of the general formula VI are then reacted according to (d) with ammonia or the salts thereof, with or without a solvent, for example alcohol, optionally at pressures of up to 150 atmospheres gauge, at temperatures between 50° and 200° C, to compounds of the general formula I. Or, the process is carried out under the conditions described in U.S. Pat. No. 3,480,634.

The reaction according to method (e) succeeds under the conditions indicated for method (a).

Amino-acid derivatives VIII and hydroxycarboxylic acid derivatives IX, which can be obtained by one of the usual methods, may be cyclized with or without acid catalysts, for example sulfuric acid or phosphoric acid, or with or without dehydratating agents, for example acetic acid anhydride or thionyl chloride, with or without solvents, for example glacial acetic acid, alcohol or ether, at temperatures in the range of from room temperature to the boiling temperature of the solvent.

When preparing the products of the invention according to method (g), the process is preferably started from derivatives of isocyanic acid or isothiocyanic acid, for example urethanes or thiourethanes of the formula XIX

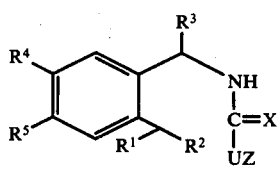

(XIX)

(X = O,S), which are reacted, for example with n-butyl-lithium to the metal organyles of the formula X.

Particularly suitable derivatives are the carbamic acid or thio-carbamic acid esters, in which X is oxygen or sulfur, U is oxygen and Z is low molecular alkyl, the thio- or di-thio-carbamic acid esters, in which X is oxygen or sulfur, U is sulfur and Z is lower alkyl or phenyl, and urea derivatives or thio-urea derivatives, in which U is the NH-group and Z is lower alkyl or phenyl.

Cyclization of X to I is suitably carried out at elevated temperatures in inert solvents, for example benzene, toluene, dimethoxyethane, at room temperature up to the boiling temperature of the solvent.

During cyclization, UZ is split off.

In the reaction of compounds II with aromatic aldehydes III there may form, under the conditions mentioned for method (a), the compounds of the formula XI as intermediate products, which, however, are not isolated, but pass into the compounds of the formula I with elimination of a phenylacetic acid amide or - thioamide.

The compounds of the general formula XI, which are used in method (h), may be prepared and isolated in another way. For this purpose, the compounds II and the aldehyde III are heated with or without a solvent, for example alcohols, benzene, or chloroform, during which time the reaction water that has formed is continuously separated.

The compounds of the formula XI are converted into compounds of the formula I by acid catalysis, it being possible to work with a solvent, for example benzene, a halogenated hydrocarbon or an alcohol, or without solvent, or to use polyphosphoric acid or other mineral acids, for example hydrochloric acid or sulfuric acid, or Lewis acids, for example BF$_3$, or other acid catalysts, for example POCl$_3$.

The subsequent introduction of the substituents R$^1$ and/or R$^2$ into the isoquinoline molecule XX

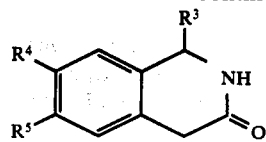

(XX)

is carried out according to known methods, by protecting the amide function, for example with a suitable reagent such as chloroformic acid ester under alkylating conditions, for example with alcoholate in alcohol or sodium amide in inert solvents, for example benzene (XXI). Then, the substituents R$^1$ and R$^2$ may be introduced into XXI

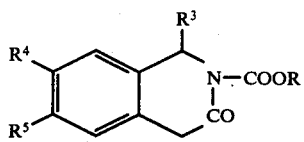

(XXI)

by a step-wise alkylation, for example with sodium amide in inert solvents, for example benzene or toluene, it being without importance whether the substitution is carried out first with R$^1$ or with R$^2$. The following hydrolysis and decarboxylation, for example by a treatment with acids or bases in water, alcohols or aqueous alcohols yields the compounds of the formula I.

The reaction according to method(k), Y in XII preferably being a halogen atom such as Cl or I, or another radical which is replaceable by a secondary amine, for example the tosyl or mesyl radical, is effected in the presence of an excess of the secondary amine to be used, or, if the secondary amine is added in stoichiometric amounts, with addition of a base, preferably sodium hydroxide solution, aqueous sodium carbonate solution, triethylamine or alcoholate, in suitable solvents, for example, water, alcohols such as methanol or butanol, ethers such as diethyl ether or dimethoxyethylene, aromatic or aliphatic, optionally halogenated hydrocarbons such as cyclohexane, chloroform, toluene or chlorobenzene, polar solvents such as dimethylsulfoxide or dimethylformamide or mixtures of the mentioned solvents, at a temperature between room temperature and the boiling temperature of the solvent used.

Alkylation of a compound of the formula XIII according to method (1) may be carried according to known methods, the alkylation with an alkyl ester of a mineral or organic acid, for example dimethyl- or diethyl-sulfate or a benzenesulfonic acid alkyl ester being preferably employed (cf. Org. Synth. 44, 72 (1964), Pharm. Chem. J. 193, (1969)), or by subjecting a compound of the formula XII to a reaction with a corresponding alkyl compound while applying the conditions specified for method (k). It is also possible to introduce the two alkyl radicals successively. Thus, the amine may be reacted with an aldehyde or ketone to a Schiff's base, the Schiff's base is alkylated and the ammonium salt is hydrogenated. It is suitable to work according to the method descibed in Chem. Inform. 16-258 (1973).

The compounds of the formula XIV are cyclized according to the usual methods. The cyclization may be carried out in the presence of a catalyst, but also without catalyst. It may be carried out in an inert solvent or without solvent. This is suitably done by keeping a compound of the formula II in an inert solvent in the presence of an acid catalyst, preferably boron trifluoride etherate or p-toluene-sulfonic acid until completion of the reaction at temperatures between 0° C and the boiling temperature of the solvent used. As solvents, there may be used preferably ethers such as tetrahydrofurane, dimethoxyethane or, optionally also chlorinated aliphatic or aromatic hydrocarbons such as cyclohexane, methylene chloride, chlorobenzene or toluene.

If Y and/or Z represent the hydroxy group, the reaction water that has formed is separated preferably by means of a water separator.

The reaction according to method (n), Y and Z in XIV preferably being a halogen atom such as Cl or I, or another radical which is replaceable by a primary amine, for example the tosyl or mesyl radical, is carried out in the presence of an excess of the primary amine or water to be used, or if the reagent is used in a stoichiometric amount, with addition of a base such as, preferably sodium hydroxide solution, aqueous sodium carbonate solution, triethylamine or alcoholate in suitable solvents, for example water, alcohols such as methanol or butanol, ethers such as diethyl ether or dimethoxyethylene, aromatic or aliphatic, optionally halogenated hydrocarbons such as cyclohexane, chloroform, toluene or chlorobenzene, polar solvents such as dimethyl-sulfoxide or dimethylformamide or mixtures of the mentioned solvents at a temperature between room temperature and the boiling temperature of the solvent used.

For converting the compounds of the formula I (X = O) into the corresponding sulfur derivatives, known reactions are employed. Particularly suitable is the reaction with $P_4S_{10}$ in pyridine or toluene with or without the addition of an acid-binding agent, for example CaO, or I (X = O) is reacted with $PCl_5$ in pyridine, benzene or toluene to the imide-chloride which yields with $H_2S$ or a thio-urea, optionally after hydrolysis of the intermediately formed is thiouronium salt, compounds of the formula I (X = S).

For converting thioamides into the corresponding amides, known methods are used. A reaction with an alkyl halide, which may also be substituted basically, is also suitable, in which the thione of the formula I reacts formally in its tautomeric imino form. The operation is carried out optionally in the presence of a base, for example potassium carbonate, in an inert solvent such as benzene, toluene, xylene, acetone or methylethyl ketone at elevated temperature, whereupon a S-alkyl compound is obtained which is de-sulfurized with mineral acid, for example hydrochloric acid, at elevated temperature. The thione of the formula I may also be directly converted into the ketone with mineral acid at elevated temperature. Furthermore, the compounds of the general formula I may be de-sulfurized with a peroxide, for example $Na_2O_2$ in an alkaline medium to the desired O-compounds I. 3,4-Dihydro-2H-isoquinoline-1-thiones may also be oxidized with $SeO_2$ in alcohol at elevated temperature to the oxygen compounds. Furthermore, the sulfur compounds may also be converted with alkali metal hexacyanoferrate-(III) in ethanol or with silver nitrate in aqueous alcohol into the corresponding oxygen compounds (cf. R. Boudet Bl. /5/, 18, 846 (1951).

As compounds of the invention, there may be prepared, in addition to the compounds specified in the Examples, preferably also the following compounds:

1-(3-aminophenyl)-4-(2-N,N-diethylaminoethyl)-6,7-dimethoxy-1,4-dihydro-2H-isoquinoline-3-one 1-(2-aminophenyl)-4-(2-N,N-diethylaminoethyl)-6,7-dimethoxy-1,4-dihydro-2H-isoquinoline-3-one 1-(4-chloro-3-aminophenyl)-4-(2-N,N-diethylaminoethyl)-6,7-dimethoxy-1,4-dihydro-2H-isoquinoline-3-one 1-(5-chloro-2-aminophenyl)-4-(2N,N-diethylaminoethyl)-6,7-dimethoxy-1,4-dihydro-2H-isoquinoline-3-one 1-(2-chloro-5-aminophenyl)-4-(2-N,N-diethylaminoethyl)-6,7-dimethoxy-1,4-dihydro-2H-isoquinoline-3-one 1-(2-chloro-6-aminophenyl)-4-(2-N,N-diethylaminoethyl)-6,7-dimethoxy-1,4-dihydro-2H-isoquinoline-3-one 1-(4-aminophenyl)-4-(2-N,N-diisopropylaminoethyl)-6,7-dimethoxy-1,4-dihydro-2H-isoquinoline-3-one 1-(3-aminophenyl)-4-(2-N,N-diisopropylaminoethyl)-6,7-dimethoxy-1,4-dihydro-2H-isoquinoline-3-one 1-(2-aminophenyl)-4-(2-N,N-diisopropylaminoethyl)-6,7-dimethoxy-1,4-dihydro-2H-isoquinoline-3-one 1-(4-chloro-3-aminophenyl)-4-(2-N,N-diisopropylaminoethyl)-6,7-dimethoxy-1,4-dihydro-2H-isoquinoline-3-one 1-(5-chloro-2-aminophenyl)-4-(2-N,N-diisopropylaminoethyl)-6,7-dimethoxy-1,4-dihydro-2H-isoquinoline-3-one 1-(2-chloro-5-aminophenyl)-4-(2-N,N-diisopropylaminoethyl)-6,7-dimethoxy-1,4-dihydro-2H-isoquinoline-3-one 1-(2-chloro-6-aminophenyl)-4-(2-N,N-diisopropylaminoethyl)-6,7-dimethoxy-1,4-dihydro-2H-isoquinoline-3-one 1-(4-aminophenyl)-4-[2-(1-piperidino)-ethyl]-6,7-dimethoxy-1,4-dihydro-2H-isoquinoline-3-one 1-(3-aminophenyl)-4-[2-(1-piperidino)-ethyl]-6,7-dimethoxy-1,4-dihydro-2H-isoquinoline-3-one 1-(2-aminophenyl)-4-[2-(1-piperidino)-ethyl]-6,7-dimethoxy-1,4-dihydro-2H-isoquinoline-3-one 1-(4-chloro-3-aminophenyl)-4-[2-(1-piperidino)-ethyl]-6,7-dimethoxy-1,4-dihydro-2H-isoquinoline-3-one 1-(5-chloro-2-aminophenyl)-4-[2-(1-piperidino)-ethyl]-6,7-dimethoxy-1,4-dihydro-2H-isoquinoline-3-one 1-(2-chloro-5-aminophenyl)-4-[2-(1-piperidino-ethyl]-6,7-dimethoxy-1,4-dihydro-2H-isoquinoline-3-one 1-(2-chloro-6-aminophenyl)-4-[2-(1-piperidino)-ethyl]-6,7-dimethoxy-1,4-dihydro-2H-isoquinoline-3-one 1-(3-aminophenyl)-4-[2-N,N-diethylaminoethyl)-1,4-dihydro-2H-isoquinoline-3-one 1-(2-aminophenyl)-4-(2-N,N-diethylaminoethyl)-1,4-dihydro-2H-isoquinoline-3-one 1-(4-chloro-3-aminophenyl)-4-(2-N,N-diethylaminoethyl)-1,4-dihydro-2H-isoquinoline-3-one 1-(5-chloro-2-aminophenyl)-4-(2-N,N-diethylaminoethyl)-1,4-dihydro-2H-isoquinoline-3-one 1-(2-chloro-5-aminophenyl)-4-(2-N,N-diethylaminoethyl)-1,4-dihydro-2H-isoquinoline-3-one 1-(2-chloro-6-aminophenyl)-4-(2-N,N-diethylaminoethyl)-1,4-dihydro-2H-isoquinoline-3-one 1-(4-aminophenyl)-4-(2-N,N-diisopropylaminoethyl)-1,4-dihydro-2H-isoquinoline-3-one 1-(3-aminophenyl)-4-(2-N,N-diisopropylaminoethyl)-1,4-dihydro-2H-isoquinoline-3-one 1-(2-aminophenyl)-4-(2-N,N-diisopropylaminoethyl)-1,4-dihydro-2H-isoquinoline-3-one 1-(4-chloro-3-aminophenyl)-4-(2-N,N-diisopropylaminoethyl)-1,4-dihydro-2H-isoquinoline-3-one
1-(5-chloro-2-aminophenyl)-4-(2-N,N-diisopropylaminoethyl)-1,4-dihydro-2H-isoquinoline-3-one
1-(2-chloro-5-aminophenyl)-4-(2-N,N-diisopropylaminoethyl)-1,4-dihydro-2H-isoquinoline-3-one
1-(2-chloro-6-aminophenyl)-4-(2-N,N-diisopropylaminoethyl)-1,4-dihydro-2H-isoquinoline-3-one
1-(4-aminophenyl)-4-[2-(1-piperidino)-ethyl]-1,4-dihydro-2H-isoquinoline-3-one
1-(3-aminophenyl)-4-[2-(1-piperidino)-ethyl]-1,4-dihydro-2H-isoquinoline-3-one
1-(2-aminophenyl)-4-[2-(1-piperidino)-ethyl]-1,4-dihydro-2H-isoquinoline-3-one
1-(4-chloro-3-aminophenyl)-4-[2-(1-piperidino)-ethyl]-1,4-dihydro-2H-isoquinoline-3-one
1-(5-chloro-2-aminophenyl)-4-[2-(1-piperidino)-ethyl]-1,4-dihydro-2H-isoquinoline-3-one
1-(2-chloro-5-aminophenyl)-4-[2-(1-piperidino)-ethyl]-1,4-dihydro-2H-isoquinoline-3-one
1-(2-chloro-6-aminophenyl)-4-[2-(1-piperidino)-ethyl]-1,4-dihydro-2H-isoquinoline-3-one
1-(4-aminophenyl)-4-[2-(morpholine-4-yl)-ethyl]-1,4-dihydro-2H-isoquinoline-3-one
1-(3-aminophenyl)-4-[2-(morpholine-4-yl)-ethyl]-1,4-dihydro-2H-isoquinoline-3-one
1-(2-aminophenyl)-4-[2-(morpholine-4-yl)-ethyl]-1,4-dihydro-2H-isoquinoline-3-one
1-(4-chloro-3-aminophenyl)-4-[2(morpholine-4-yl)-ethyl]-1,4-dihydro-2H-isoquinoline-3-one
1-(5-chloro-2-aminophenyl)-4-[2-(morpholine-4-yl)-ethyl]-1,4-dihydro-2H-isoquinoline-3-one
1-chloro-5-aminophenyl)-4-[2-(morpholine-4-yl)-ethyl]-1,4-dihydro-2H-isoquinoline-3-one
1-(2-chloro-6-aminophenyl)-4-[2-(morpholine-4-yl)-ethyl]-1,4-dihydro-2H-isoquinoline-3-one
1-(4-aminophenyl)-4-[2-(1-methyl-piperazine-4-yl)-ethyl]-1,4-dihydro-2H-isoquinoline-3-one
1-(3-aminophenyl-4-[2-(1-methyl-piperazine-4-yl)-ethyl]-1,4-dihydro-2H-isoquinoline-3-one
1-(2-aminophenyl)-4-[2-(1-methyl-piperazine-4-yl)-ethyl]-1,4-dihydro-2H-isoquinoline-3-one
1-(4-chloro-3-aminophenyl)-4-[2-(1-methyl-piperazine-4-yl)-ethyl]-1,4-dihydro-2H-isoquinoline-3-one
1-(5-chloro-2-aminophenyl)-4-[2-(1-methyl-piperazine-4-yl)-ethyl]-1,4-dihydro-2H-isoquinoline-3-one
1-(2-chloro-5-aminophenyl)-4-[2-(1-methyl-piperazine-4-yl)-ethyl]-1,4-dihydro-2H-isoquinoline-3-one
1-(2-chloro-6-aminophenyl)-4-[2-(1-methyl-piperazine-4-yl)-ethyl]-1,4-dihydro-2H-isoquinoline-3-one
1-(4-aminophenyl)-4-[2-(1-phenyl-piperazine-4-yl)-ethyl]-1,1-dihydro-2H-isoquinoline-3-one
1-(3-aminophenyl)-4-[2-(1-phenyl-piperazine-4-yl)-ethyl]-1,4-dihydro-2H-isoquinoline-3-one
1-(2-aminophenyl)-4-[2-(1-phenyl-piperazine-4-yl)-ethyl]-1,4-dihydro-2H-isoquinoline-3-one
1-(4-chloro-3-aminophenyl)-4-[2-(1-phenyl-piperazine-4-yl)-ethyl]-1,4-dihydro-2H-isoquinoline-3-one
1-(5-chloro-2-aminophenyl)-4-[2-(1-phenyl-piperazine-4-yl)-ethyl]-1,4-dihydro-2H-isoquinoline-3-one
1-(2-chloro-5-aminophenyl)-4-[2-(1-phenyl-piperazine-4-yl)-ethyl]-1,4-dihydro-2H-isoquinoline-3-one
1-(2-chloro-6-aminophenyl)-4-[2-(1-phenyl-piperazine-4-yl)-ethyl]-1,4-dihydro-2H-isoquinoline-3-one
1-(4-chlorophenyl)-4-[2-(1-phenyl-piperazine-4-yl)-ethyl]-1,4-dihydro-2H-isoquinoline-3-one
1-(3-chlorophenyl)-4-[2-(1-phenyl-piperazine-4-yl)-ethyl]-1,4-dihydro-2H-isoquinoline-3-one
1-(2-chlorophenyl)-4-[2-(1-phenyl-piperazine-4-yl)-ethyl]-1,4-dihydro-2H-isoquinoline-3-one
1-phenyl-4-[2-(1-phenyl-piperazine-4-yl)-ethyl]-1,4-dihydro-2H-isoquinoline-3-one
1-(4-chlorophenyl)-4-[2-(1-methyl-piperazine-4-yl)-ethyl]-1,4-dihydro-2H-isoquinoline-3-one
1-(3-chlorophenyl)-4-[2-(1-methyl-piperazine-4-yl)-ethyl]-1,4-dihydro-2H-isoquinoline-3-one
1-(2-chlorophenyl)-4-[2-(1-methyl-piperazine-4-yl)-ethyl]-1,4-dihydro-2H-isoquinoline-3-one
1-phenyl-4-[2-(1-methyl-piperazine-4-yl)-ethyl]-1,4-dihydro-2H-isoquinoline-3-one
1-(4-aminophenyl)-4-[2-(thiomorpholinyl)-ethyl]-1,4 dihydro-2H-isoquinoline-3-one
1-(3-aminophenyl)-4-[2-(thiomorpholinyl)-ethyl]-1,4 dihydro-2H-isoquinoline-3-one
1-(2-aminophenyl)-4-[2-(thiomorpholinyl)-ethyl]-1,4 dihydro-2H-isoquinoline-3-one
1-(4-chloro-3-aminophenyl)-3-[2-(thiomorpholinyl)-ethyl]-1,4-dihydro-2H-isoquinoline-3-one
1-(5-chloro-2-aminophenyl)-4-[2-(thiomorpholinyl)-ethyl]-1,4-dihydro-2H-isoquinoline-3-one
1-(2-chloro-5-aminophenyl)-4-[2-(thiomorpholinyl)-ethyl]-1,4-dihydro-2H-isoquinoline-3-one
1-(2-chloro-6-aminophenyl)-4-[2-(thiomorpholinyl)-ethyl]-1,4-dihydro-2H-isoquinoline-3-one
1-(4-aminophenyl)-4-[2-(1-phenyl-piperazine-4-yl)-ethyl]-1,4-dihydro-2H-isoquinoline-3-thione
1-(3-aminophenyl)-4-[2-(1-phenyl-piperazine-4-yl)-ethyl]-1,4-dihydro-2H-isoquinoline-3-thione
1-(2-aminophenyl)-4-[2-(1-phenyl-piperazine-4-yl)ethyl]-1,4-dihydro-2H-isoquinoline-3-thione
1-(4-chloro-3-aminophenyl)-4-[2-(1-phenyl-piperazine-4-yl)-ethyl]-1,4-dihydro-2H-isoquinoline-3-thione
1-(5-chloro-3-aminophenyl)-4-[2-(1-phenyl-piperazine-4-yl)-ethyl]-1,4-dihydro-2H-isoquinoline-3-thione
1-(2-chloro-5-aminophenyl)-4-[2-(1-phenyl-piperazine-4-yl)-ethyl]-1,4-dihydro-2H-isoquinoline-3-thione
1-(2-chloro-6-aminophenyl)-4-[2-(1-phenyl-piperazine-4-yl)-ethyl]-1,4-dihydro-2H-isoquinoline-3-thione
1-(4-chlorophenyl)--[2-(1-phenyl-piperazine-4-yl)-ethyl]-1,4-dihydro-2H-isoquinoline-3-thione
1-(3-chlorophenyl)-4-[2-(1-phenyl-piperazine-4-yl)-ethyl]-1,4-dihydro-2H-isoquinoline-3-thione
1-(2-chlorophenyl)-4-[2-(1-phenyl-piperazine-4-yl)-ethyl]-1,4-dihydro-2H-isoquinoline-3-thione
1-phenyl-4-[2-(1-phenyl-piperazine-4-yl)-ethyl]-ethyl]-1,4-dihydro-2H-isoquinoline-3-thione
1-(4-chlorophenyl)-4-[2-(1-methyl-piperazine-4-yl)-ethyl]-1,4-dihydro-2H-isoquinoline-3-thione
1-(3-chlorophenyl)-4-[2-(1-methyl-piperazine-4-yl)-ethyl]-1,4-dihydro-2H-isoquinoline-3-thione
1-(2-chlorophenyl)-4-[2-(1-methyl-piperazine-4-yl)-ethyl]-1,4-dihydro-2H-isoquinoline-3-thione
1-phenyl-4-[2-(1-methyl-piperazine-4-yl)-ethyl]-1,4-dihydro-2H-isoquinoline-3-thione
1-(4-aminophenyl)-4-[2-(morpholine-4-yl)-ethyl]-1,4-dihydro-2H-isoquinoline-3-thione
1-(3-aminophenyl)-4-[2-(morpholine-4-yl)-ethyl]-1,4-dihydro-2H-isoquinoline-3-thione 1-(2-aminophenyl)-4-[2-(morpholine-4-yl)-ethyl]-1,4-dihydro-2H-isoquinoline-3-thione 1-(4-chloro-3-aminophenyl)-4-[2-(morpholine-4-yl)-ethyl]-1,4-dihydro-2H-isoquinoline-3-thione 1-(5-chloro-2-aminophenyl)-4-[2-(morpholine-4-yl)-ethyl]-1,4-dihydro-2H-isoquinoline-3-thione 1-(2-chloro-5-aminophenyl)-4-[2-(morpholine-4-yl)-ethyl]-1,4-dihydro-2H-isoquinoline-3-thione 1-(2-chloro-6-aminophenyl)-4-[2-(morpholine-4-yl)-ethyl]-1,4-dihydro-2H-isoquinoline-3-thione 1-(4-aminophenyl)-4-[2-(1-methyl-piperazine-4-yl)-ethyl]-1,4-dihydro-2H-isoquinoline-3-thione 1-(3-aminophenyl)-4-(1-methyl-piperazine-4-yl)-ethyl]-1,4-dihydro-2H-isoquinoline-3-thione 1-(2-aminophenyl)-4-[2-(1-methyl-piperazine-4-yl)-ethyl]-1,4-dihydro-2H-isoquinoline-3-thione 1-(4-chloro-3-aminophenyl)-4-[2-(1-methyl-piperazine-4-yl)-ethyl]-1,4-dihydro-2H-isoquinoline-3-thione 1-(5-chloro-2-aminophenyl)-4-[2-(1-methyl-piperazine-4-yl)-ethyl]-1,4-dihydro-2H-isoquinoline-3-thione 1-(2-chloro-3-aminophenyl)-4-[2-(1-methyl-piperazine-4-yl)-ethyl]-1,4-dihydro-2H-isoquinoline-3-thione 1-(2-chloro-6-aminophenyl)-4-[2-(1-methyl-piperazine-4-yl)-ethyl]-1,4-dihydro-2H-isoquinoline-3-thione 1-(4-aminophenyl)-4-[2-(thiomorpholinyl)-ethyl]-1,4-dihydro-2H-isoquinoline-3-thione 1-(3-aminophenyl)-4[2-(thiomorpholinyl)-ethyl]-1,4-dihydro-2H-isoquinoline-3-thione 1-(2-aminophenyl)-4-[2-(thiomorpholinyl)-ethyl]-1,4-dihydro-2H-isoquinoline-3-thione 1-(4-chloro-3-aminophenyl)-4-[2-(thiomorpholinyl)-ethyl]-1,4-dihydro-2H-isoquinoline-3-thione 1-(5-chloro-2-aminophenyl)-4-[2-(thiomorpholinyl)-ethyl]-1,4-dihydro-2H-isoquinoline-3-thione 1-(2-chloro-5-aminophenyl)-4-[2-(thiomorpholinyl)-ethyl]-1,4-dihydro-2H-isoquinoline-3-thione 1-(2-chloro-6-aminophenyl)-4-[2-(thiomorpholinyl)-ethyl]-1,4-dihydro-2H-isoquinoline-3-thione The compounds of the invention possess valuable therapeutic properties. In addition to other pharmacological properties, they have a favorable action on the coronary circulation, which is marked especially by an anti-arrhythmic activity. Therefore, the compounds of the invention may be used in the treatment of disorders of the heart rhythm. The anti-arrhythmic action was proved on isolation papillary muscles of Guinea pigs and on strophantine-poisoned dogs.

The novel compounds may be administered alone or in admixture with pharmacologically tolerated carriers. For a form suitable for oral administration, the active compounds are mixed with known substances and brought by known methods into forms which are suitable for oral administration, for example tablets, capsules, aqueous, alcoholic or oily suspensions or aqueous, alcoholic or oily solutions. As inert carriers, there may be used, for example magnesium carbonate lactose or maize starch with addition of other substances, for example magnesium stearate. Confectioning may be carried out with a dry or wet granulation. As oily carriers or solvents, there may be used in particular oils of vegetable or animal origin, for example sunflower oil or cod-liver oil.

A particular form of administration of the compounds of the invention is intravenous administration. For a form suitable for intravenous administration, the active compounds or their physiologically tolerated salts together with other known substances are brought into solution. The physiologically tolerated salts are formed, for example with the following acids: hydrochloric acid, hydrobromic acid, hydriodic acid, phosphoric acid, sulfuric acid, methyl-sulfuric acid, amido-sulfonic acid, nitric acid, formic acid, acetic acid, propionic acid, succinic acid, tartaric acid, lactic acid, malonic acid, fumaric acid, citric acid, malic acid, mucic acid, benzoic acid, salicyclic acid, aceturic acid, embonic acid, naphthalene-1,3-disulfonic acid, ascorbic acid, phenyl-acetic acid, p-amino-salicylic acid, hydroxy-ethane-sulfonic acid, benzene-sulfonic acid or synthetic resins which contain acidic groups, for example those having an ion-exchanging action.

As solvents for the corresponding physiologically tolerated salts of the active compounds to give a form suitable for intravenous administration, there may be used, for example, water, physiological salt solution or alcohols such as ethanol, propanediol or glycerine, furthermore sugar solutions, for example glucose or mannitose solutions, or also mixtures of the various solvents mentioned.

The single dose for peroral administration is 50–500 mg, preferably 100 mg, for intravenous or intramuscular administration 20–100 mg, preferably 50 mg. The daily dose with peroral administration is 50–1000 mg, preferably 300 mg, and with intravenous or intramuscular administration 20–500 mg, preferably 100 mg.

The following Examples illustrate the invention:

EXAMPLES 1. 1-(4-chlorophenyl)-4-(3-N,N-dimethylamino-2-methyl-propyl)-1,4-dihydro-2H-isoquinoline-3-one 50 ml of 85% of polyphosphoric acid and 50 g of phosphorus pentoxide were mixed with one another and 0.1 mole of 2-cyano-1-phenyl-3-(N,N-dimethylaminomethyl)-butane was added at room temperature. The reaction mixture was heated to 80° C and 0.04 mole of 4-chlorobenzaldehyde was added. The whole was heated for 1 hour to 100° C and 0.04 mole of 4-chlorobenzaldehyde was again added. After a further hour at 100° C, the reaction mixture was poured into 1 liter of water, adjusted to pH 10 with concentrated ammonia. The crystal magma was filtered off with suction and recrystallized from ethanol. M.p. 253° C.

2.

1-(4-chlorophenyl)-4-[2-(1-pyrrolidino)-ethyl]-1,4-dihydro-2H-isoquinoline-3-one From 1-cyano-1-phenyl-3-(1-pyrrolidino)-propane and 4-chlorobenzaldehyde in a manner analogous to that described in Example 1.

M.p. 165°–166° C (HCl salt).

3.

1-(4-chlorophenyl)-4-(2-N,N-diethylaminoethyl)-1,4-dihydro-2H-isoquinoline-3-one From 1-cyano-1-phenyl-3-(N,N-diethylamino)-propane and 4-chlorobenzaldehyde in a manner analogous to that described in Example 1.

M.p: 148°–150° C (HCl salt)

4.
1-(4-chlorophenyl)-4-(3-N,N-dimethylaminopropyl)-1,4-dihydro-2H-isoquinoline-3-thione a. 20 millimoles of 1-(4-chlorpheyl)-4-(3-N,N-dimethyl aminopropyl)-1,4-dihydro-2H-isoquinoline-3-one were introduced into a suspension of 20 millimoles of phosphorus pentachloride in 20 ml of toluene and boiled for 3 hours under reflux.

Then, H₂S was introduced at room temperature until the development of HCl ceased.

The solvent was removed under reduced pressure and the residue was recrystallized from ethanol.

M.P.: 238°–240° C.

b. 20 millimole of 1-(4-chlorophenyl)-4(3-N,N-dimethylaminopropyl)-1,4-dihydro-2H-isoquinoline-1-one were introduced, while stirring, into a suspension of 8 millimoles of phosphorus penta-sulfide and 32 millimoles of calcium oxide in 50 ml of toluene and the whole was heated for 15 hours under reflux. The hot toluene solution was poured through a filter to remove the residue and the resin was extracted twice with 50 ml portions of benzene. The combined organic solutions were concentrated under reduced pressure and the remaining oil was recrystallized from ethanol.

M.p. 237°–238° C.

c. 90 Millimoles of 1-(4-chlorophenyl)-4(3-N,N-dimethylaminopropyl)-1,4-dihydro-2H-isoquinoline-3-one were dissolved in 35 ml of pyridine and 40 millimoles of phosphorus pentasulfide were added, while stirring. The solution was heated for 4 hours under reflux and, after having cooled, it was poured into 400 ml of water. The pH value was adjusted to 8–8.5 with 10% potassium hydroxide solution and the whole was stirred for 4 hours. After filtration with suction, the product was washed with water, dried in air and recrystallized from ethanol.

M.p.: 237°–240° C.

5.
1-(4-chlorophenyl)-4-ethyl-4-[2-(1-piperidino)-ethyl]-1,4-dihydro-2H-isoquinoline-3-one From 3-cyano-3-phenyl-5-(1-piperidino)-pentane and 4-chlorobenzaldehyde in a manner analogous to that described in Example 1.

M.p.: 240°–242° C (HCl salt)

6.
1-(4-chlorophenyl)-4-[2-(1-piperidino)-ethyl]-1,4-dihydro-2H-isoquinoline-3-one From 1-cyano-1-phenyl-3-(1-piperidino)-propane and 4-chlorobenzaldehyde in a manner analogous to that described in Example 1.

M.p.: 172°–175° C (HCl salt)

7.
1-(4-chlorophenyl)-4-(3-N,N-dimethylamino-propyl)-1,4-dihydro-2H-isoquinoline-3-one From 1-cyano-1-phenyl-4-(N,N-dimethylamino)-butane and 4-chlorobenzaldehyde in a manner analogous to that described in Example 1.

M.p.: 157°–158° C 8.
1-phenyl-4-[2-(1-pyrrolidino)-ethyl]-1,4-dihydro-2H-isoquinoline-3-one From 1-cyano-1-phenyl-3-(1-pyrrolidino)-propane and benzaldehyde in a manner analogous to that described in Example 1.

M.p.: 224°–227° C (HCl salt)

9.
1-phenyl-4-(2-N,N-diethylaminoethyl)-1,4-dihydro-2H-isoquinoline-3-one

From 1-cyano-1-phenyl-3-diethylamino-propane and benzaldehyde in a manner analogous to that described in Example 1.

M.p.: 176°–179° C. (HCl salt)

10.
1-(4-chlorophenyl)-4-ethyl-(3-N,N-dimethylaminopropyl)-1,4-dihydro-2H-isoquinoline-3-one From 3-cyano-3-phenyl-6-dimethylamino-hexane and 4-chlorobenzaldehyde in a manner analogous to that described in Example 1.

M.p.: 156°–159° C.

11.
1-(4-chlorophenyl)-4-ethyl-4-(2-N,N-diethylaminoethyl)-1,4-dihydro-2H-isoquinoline-3-one From 3-cyano-3-phenyl-5-diethylamino-pentane and 4-chlorobenzaldehyde in a manner analogous to that described in Example 1.

M.p.: 120° C.

12.
1-(4-chlorophenyl)-4-n-butyl-4-(3-N,N-dimethylaminopropyl)-1,4-dihydro-2H-isoquinoline-3-one From 5-cyano-5-phenyl-8-dimethylamino-octane and 4-chlorobenzaldehyde in a manner analogous to that described in Example 1.

M.p.: 170°–172° C.

13.
1-(4-chlorophenyl)-4-n-butyl-4-[2-(1-piperidino)-ethyl]-1,4-dihydro-2H-isoquinoline-3-one From 5-cyano-5-phenyl-7-(1-piperidino)-heptane and 4-chlorobenzaldehyde in a manner analogous to that described in Example 1.

M.p.: 138°–143° C.

14.
1-(4-chlorophenyl)-4-methyl-4-[2-(1-piperidino)-ethyl]-1,4-dihydro-2H-isoquinoline-3-one From 2-cyano-2-phenyl-4-(1piperidino)-butane and 4-chlorobenzaldehyde in a manner analogous to that described in Example 1.

M.p.: 193°–196° C.

15.
1-(4-chlorophenyl)-4-methyl-4-(3-N,N-dimethylaminopropyl)-1,4-dihydro-2H-isoquinoline-3-one From 2-cyano-2-phenyl-5-dimethylamino-pentane and 4-chlorobenzaldehyde in a manner analogous to that described in Example 1.

M.p.: 227°–229° C.

16.
1-(4-chlorophenyl)-4-methyl-4-(2-N,N-diisopropylaminoethyl)-1,4-dihydro-2H-isoquinoline-3-one From 2-cyano-2-phenyl-4-diisopropylamino-butane and 4-chlorobenzaldehyde in a manner analogous to that described in Example 1.
M.p.: 112°-114° C.

17.
1-(4-chlorophenyl)-4-methyl-4-(2-N,N-diethylaminoethyl)-1,4-dihydro-2H-isoquinoline-3-one From 2-cyano-2-phenyl-4-diethylamino-butane and 4-chlorobenzaldehyde in a manner analogous to that described in Example 1.
M.p.: 122°-123° C.

18.
1-(4-chlorophenyl)-4-(2-N,N-diisopropylaminoethyl)-1,4-dihydro-2H-isoquinoline-3-one From 1-cyano-1-phenyl-3-diisopropylamino-propane and 4-chlorobenzaldehyde in a manner analogous to that described in Example 1.
M.p.: 202°-205° C (HCl salt)

19.
1-(2-chlorophenyl)-4-(2-N,N-diethylaminoethyl)-1,4-dihydro-2H-isoquinoline-3-one From 1-cyano-1-phenyl-3-diethylamino-propane and 2-chlorobenzaldehyde in a manner analogous to that described in Example 1.
M.p.: 100°-103° C (HCl salt)

20.
1-(2,4-dichlorophenyl)-4-(2-N,N-diethylaminoethyl)-1,4-dihydro-2H-isoquinoline-3-one From 1-cyano-1-phenyl-3-diethylamino-propane and 2,4-dichlorobenzaldehyde in a manner analogous to that described in Example 1.
M.p.: 150°-152° C.

21.
1-(4-chlorophenyl)-4-(2-N,N-dimethylaminoethyl)-1,4-dihydro-2H-isoquinoline-3-one From 1-cyano-1-phenyl-3-dimethylamino-propane and 4-chlorobenzaldehyde in a manner analogous to that described in Example 1.
M.p.: 119°-122° C.

22.
1-(4-nitrophenyl)-4-(2-N,N-diethylaminoethyl)-1,4-dihydro-2H-isoquinoline-3-one From 1-cyano-1-phenyl-3-diethylamino-propane and 4-nitrobenzaldehyde in a manner analogous to that described in Example 1.
M.p.: 138°-139° C.

23.
1-(3,4-dichlorophenyl)-4-(2-N,N-diethylaminoethyl)-1,4-dihydro-2H-isoquinoline-3-one From 1-cyano-1-phenyl-3-diethylamino-propane and 3,4-dichlorobenzaldehyde in a manner analogous to that described in Example 1.
M.p.: 133°-137° C.

24.
1-(4-methylphenyl)-4-(2-N,N-diethylaminoethyl)-1,4-dihydro-2H-isoquinoline-3-one From 1-cyano-1-phenyl-3-diethylamino-propane and 4-methylbenzaldehyde in a manner analogous to that described in Example 1.
M.p.: 113°-115° C.

25.
1-(4-aminophenyl)-4-(2-N,N-diethylaminoethyl)-1,4-dihydro-2H-isoquinoline-3-one From the compound of Example 22 by hydrogenation in methanol at 50° C/50 atmospheres gauge after 10 hours.
M.p.: 245°-248° C (HCl salt)

26.
1-(4-acetylaminophenyl)-4-(2-N,N-diethylaminoethyl)-1,4-dihydro-2H-isoquinoline-3-one From the compound of Example 25 by acylation in pyridine with acetic anhydride.
M.p.: 221°-225° C.

27.
1-(4-chlorophenyl)-4-spiro-(4-N-methylpiperidine)-1,4-dihydro-2H-isoquinoline-3-one From 4-cyano-4-phenyl-N-methylpiperidine and 4-chlorobenzaldehyde in a manner analogous to that described in Example 1.
M.p.: 243° C.

28.
1-(4-chlorophenyl)-4-(2-N,N-diethylaminoethyl)-6,7-dimethoxy-1,4-dihydro-2H-isoquinoline-3-one From 1-cyano-1-(3,4-dimethoxyphenyl)-3-diethylaminopropane and 4-chlorobenzaldehyde in a manner analogous to that described in Example 1.
M.p.: 206°-208° C.

29.
1-phenyl-4-(2-N,N-diethylaminoethyl)-6,7-dimethoxy-1,4-dihydro-2H-isoquinoline-3-one From 1-cyano-2-(3,4-dimethoxyphenyl)-3-diethylaminopropane and benzaldehyde in a manner analogous to that described in Example 1.
M.p.: 169° C.

30.
1-(4-nitrophenyl)-4-(2-N,N-diethylaminoethyl)-6,7-dimethoxy-1,4-dihydro-2H-isoquinoline-3-one From 1-cyano-1-(3,4-dimethoxyphenyl)-3-diethylaminopropane and 4-nitrobenzaldehyde in a manner analogous to that described in Example 1.
M.p.: 212°-213° C.

31.
1-(4-pyridyl)-4-(2-N,N-diethylaminoethyl)-6,7-dimethoxy-1,4-dihydro-2H-isoquinoline-3-one From 1-cyano-1-(3,4-dimethoxyphenyl)-3-diethylaminopropane and pyridine-4-aldehyde in a manner analogous to that described in Example 1.
M.p.: 171°-173° C.

32.
1-(4-aminophenyl)-4-(2-N,N-diethylaminoethyl)-6,7-dimethoxy-1,4-dihydro-2H-isoquinoline-3-one From the compound of Example 30 in a manner analogous to that described in Example 25.
M.p.: 183° C (HCl salt)

33.
1-(4-chloro-3-sulfamoylphenyl)-4-(2-N,N-diethylaminoethyl)-6,7-dimethoxy-1,4-dihydro-2H-isoquinoline-3-one From 1-cyano-2-(3,4-dimethoxyphenyl)-3-diethylaminopropane and 4-chloro-3-sulfamoylbenzaldehyde in a manner analogous to that described in Example 1.
M.p.: 175° C (HCl salt)

34.
1-(4-chlorophenyl)-4-(3-N,N-dimethylaminopropyl)-1,4-dihydro-2H-isoquinoline-3-thione 50 ml of 85 % polyphosphoric acid and 50 g of phosphorus pentoxide were mixed with one another and 0.1 mole of 2-phenyl-4-(N,N-dimethylaminomethyl)-pentane-thiocarboxylic acid amide was added at room temperature. The reaction mixture was heated to 80° C and 0.04 mole of 4-chlorobenzaldehyde was added. The whole was then heated for 1 hour to 100° C. Then, 0.04 mole of 4-chlorobenzaldehyde was added. After a further hour at 100° C, the reaction mixture was poured into 1 liter of water and the pH value was adjusted to 10 by means of concentrated ammonia. The crystal magma was filtered off with suction and recrystallized from ethanol.
M.p.: 236°–239° C.

35.
1-(4-chlorophenyl)-4-(3-N,N-dimethylamino-2-methyl-propyl)-1,4-dihydro-2H-isoquinoline-3-thione a. N,N'-4-chlorobenzylidene-bis-(2-phenyl-4-dimethylaminomethyl-pentanoic acid thioamide)

0.1 mole of 4-chlorobenzaldehyde and 0.2 mole of 2-phenyl-4-dimethylamino-methylpentanoic acid thioamide were kept for 3 hours at 110° C. After having cooled, the product was recrystallized from ethanol.
M.p.: 153° C.

b. 50 ml of 85% polyphosphoric acid and 50 g of phosphorus pentoxide were mixed and 0.1 mole of the compound prepared according to Example 35a was added at room temperature. The whole was heated for 2 hours to 100° C and poured subsequently into 1 liter of water. The pH value was adjusted to 10 by means of concentrated ammonia. The crystal magma was filtered off with suction and recrystallized from ethanol.
M.p.: 237°–240° C.

36.
1-(4-chlorophenyl)-4-(3-N,N-dimethylamino-2-methyl-propyl)-1,4-dihydro-2H-isoquinoline-3-one 0.02 mole of 1-(4-chlorophenyl)-4-(3-N,N-dimethylamino-2-methyl-propyl)-1,4-dihydro-2H-isoquinoline-3-thione was boiled under refluxed for 4 hours with 50 ml of semi-concentrated hydrochloric acid. The reaction mixture was then rendered alkaline, extracted with chloroform and the organic phase was washed once with a solution of sodium bicarbonate and then with water, dried and concentrated.
M.p.: 251°–255° C.

37.
1-(4-chlorophenyl)-4-(3-N,N-dimethylamino-2-methyl-propyl)-1,4-dihydro-2H-isoquinoline-3-one 0.02 mole of 1-(4-chlorophenyl)-4-(3-N,N-dimethylamino-2-methyl-propyl)-1,4-dihydro-2H-isoquinoline-1-thione was dissolved in 50 ml of ethanol and 0.01 mole of selenium dioxide was added. The whole was boiled for 4 hours under reflux, cooled, undissolved matter was filtered off and the solution was concentrated.
M.p.: 249°–253° C.

38.
1-(4-chlorophenyl)-4-[2-(morpholine-4-yl)-ethyl]-1,4-dihydro-2H-isoquinoline-3-one 50 ml of 85% of polyphosphoric acid and 50 g of phosphorus pentoxide were mixed and 0.1 mole of 1-cyano-1-phenyl-3-(morpholine-4-yl)-propane was added at room temperature. The reaction mixture was heated to 80° C and 0.04 mole of 4-chlorobenzaldehyde was added. The whole was heated to 100° C and 0.04 mole of 4-chlorobenzaldehyde was added. After 1 further hour at 100° C, the reaction mixture was poured into 1 liter of wate. The pH was adjusted to 10 by means of concentrated ammonia. The crystal magma was filtered off with suction and recrystallized from ethanol.
M.p.: 239°–245° C (HCl)

39.
1-(4-chlorophenyl)-4-[2-(1-methyl-piperazine-4-yl)-ethyl]-1,4-dihydro-2H-isoquinoline-3-one 50 ml of 85% polyphosphoric acid and 50 g of phosphorus pentoxide were mixed and 0.1 mole of 1-cyano-1-phenyl-3-(1-methyl-piperazine-4-yl)-propane was added. The reaction mixture was heated to 80° C and 0.04 mole of 4-chlorobenzaldehyde was added. The whole was heated for 1 hour to 100° C and 0.04 mole of 4-chlorobenzaldehyde was added. After a further hour at 100° C the mixture was poured into 1 liter of water and the pH value was adjusted to 10 by means of concentrated ammonia. The crystal magma was filtered off with suction and recrystallized from ethanol.
M.p.: 201°–205° C (oxalate)

40.
1-(4-chlorophenyl)-4-[2-(morpholine-4-yl)-ethyl]-1,4-dihydro-2H-isoquinoline-3-thione 20 millimoles of 1-(4-chlorophenyl)-4-[2-(morpholine-4-yl)-ethyl]-1,4-dihydro-2H-isoquinoline-3-one were introduced, while stirring, into a suspension of 8 millimoles of phosphorus pentasulfide and 32 millimoles of calcium oxide in 50 ml of toluene and the whole was heated for 7 hours under reflux until the reaction was completed. The reaction mixture was decanted off to remove the resinous residue and extracted twice with toluene. The combined organic solutions were concentrated and the product was recrystallized from isopropanol.
M.p.: 228°–231° C (HCl)

We claim:
1. A 1,4-dihydro-2H-isoquinoline compound of the formula

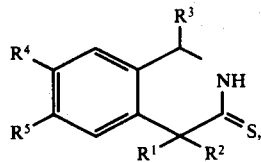

and physiologically tolerated salts thereof, wherein $R^1$ is hydrogen or straight-chain or branched alkyl of 1–6 carbon atoms; $R^2$ is morpholine-loweralkyl; $R^3$ is pyridyl, phenyl, or phenyl mono- or di-substituted by halo, nitro, amino, alkanoylamino having 1 to 4 carbon atoms or alkyl having 1 to 4 carbon atoms; and $R^4$ and $R^5$, which may be the same or different, are hydrogen or alkoxy having 1 to 4 carbon atoms.

2. The compound defined in claim 1 which is 1-(4-chlorophenyl)-4-[2-(morpholine-4-yl)-ethyl]-1,4-dihydro-2H-isoquinoline-3-thione.

3. A pharmaceutical composition for the treatment of arrhythmia comprising an anti-arrhthimically effective amount of a compound as in claim 1 in combination with a pharmacologically tolerated carrier.

4. A method for treating arrhythmia in a patient suffering therefrom which comprises administering an anti-arrhythmically effective amount of a compound as in claim 1.

* * * * *